(12) United States Patent
Palmer

(10) Patent No.: US 12,053,410 B2
(45) Date of Patent: Aug. 6, 2024

(54) SOFT-EDGED OSTOMY BAGS

(71) Applicant: Cure Medical LLC, Henderson, NV (US)

(72) Inventor: Timothy A. Palmer, Stillwater, MN (US)

(73) Assignee: CONVATEC INC., Bridgewater, NJ (US)

( * ) Notice: Subject to any disclaimer, the term of this patent is extended or adjusted under 35 U.S.C. 154(b) by 0 days.

(21) Appl. No.: 18/490,969

(22) Filed: Oct. 20, 2023

(65) Prior Publication Data
US 2024/0041636 A1 Feb. 8, 2024

Related U.S. Application Data

(63) Continuation of application No. PCT/US2022/021705, filed on Mar. 24, 2022.

(60) Provisional application No. 63/178,714, filed on Apr. 23, 2021.

(51) Int. Cl.
A61F 5/445 (2006.01)
A61F 5/44 (2006.01)
A61F 5/448 (2006.01)

(52) U.S. Cl.
CPC ............ *A61F 5/448* (2013.01); *A61F 5/4404* (2013.01); *A61F 5/445* (2013.01)

(58) Field of Classification Search
CPC ........ A61F 5/44–449; A61F 2005/4402–4495; A61J 1/10; A61J 1/12
See application file for complete search history.

(56) References Cited

U.S. PATENT DOCUMENTS

| 4,439,191 A | 3/1984 | Hogan |
| 4,710,182 A * | 12/1987 | Bryson ................... A61F 5/445 604/339 |
| 4,983,171 A | 1/1991 | Schirmer |
| 5,250,042 A | 10/1993 | Torgalkar et al. |
| 6,946,182 B1 | 9/2005 | Allgeuer et al. |
| 10,045,878 B2 | 8/2018 | Freiding |
| 10,105,254 B2 | 10/2018 | Oeelund |
| 10,322,024 B2 | 6/2019 | Chang |
| 2005/0143696 A1* | 6/2005 | Pedersen ................. A61F 5/448 604/332 |

(Continued)

FOREIGN PATENT DOCUMENTS

WO 2022225638 A1 10/2022

OTHER PUBLICATIONS

World Intellectual Property Organization, International Search Report and Written Opinion for International Application No. PCT/US22/21705, mail date Jul. 1, 2022, 16 total pages.

(Continued)

*Primary Examiner* — Susan S Su
(74) *Attorney, Agent, or Firm* — TAFT STETTINIUS & HOLLISTER LLP; Ryan O. White; Derek B. Lavender

(57) ABSTRACT

A more comfortable ostomy bag that will not irritate the skin from relative movement. The ostomy bag has a pair of flexible flat sheets of material bonded together at juxtaposed edges to form a seam. A soft outer edge outside of the seam is formed by extensions of the sheets that either remain disconnected so as to form loose flaps or are slit radially to form finger-like extensions, or both. The ostomy bag further has an inlet opening formed through one of the flat sheets.

23 Claims, 4 Drawing Sheets

(56) References Cited

U.S. PATENT DOCUMENTS

| | | | |
|---|---|---|---|
| 2005/0143697 A1 | 6/2005 | Rieslnger | |
| 2006/0258997 A1 | 11/2006 | Belt | |
| 2014/0270577 A1* | 9/2014 | Murray | B65D 31/02 |
| | | | 383/5 |
| 2017/0112658 A1* | 4/2017 | Hosono | A61F 5/445 |

OTHER PUBLICATIONS

Ostomy bag cover Ostomy Inspire product search, last accessed Jun. 22, 2020.

VeganOstomy, Coloplast Sensura Mio High-Output ostomy bags: overview; online article, www.veganostomy.ca/sensura-mio-high-output, last accessed Jun. 22, 2020.

ConcaTec, Esteem + Flex Convex, online article, www.convatec.com/ostomy/ostomy-product-infomration-flex-filter-two, last accessed Jun. 22, 2020.

* cited by examiner

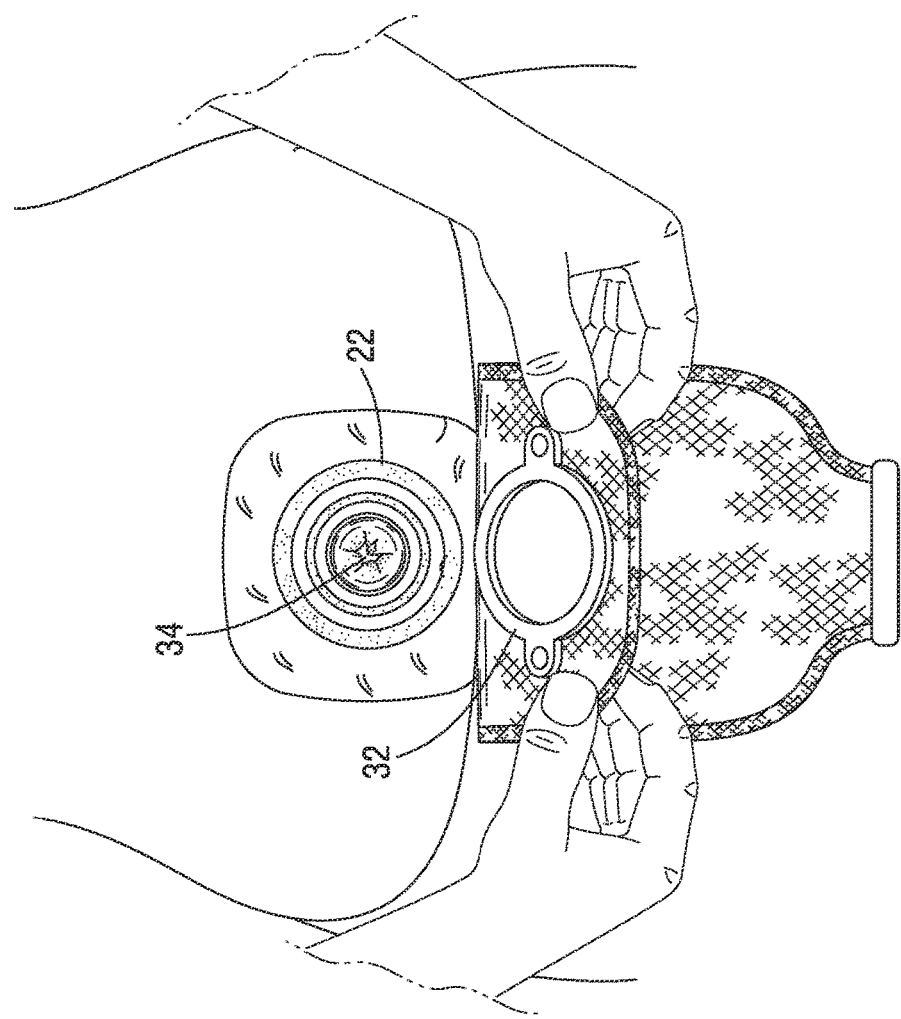
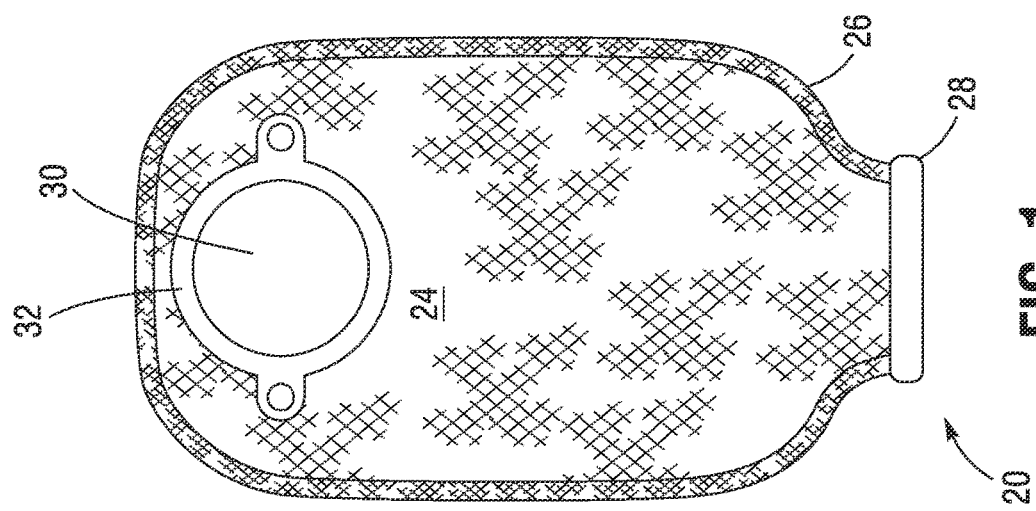

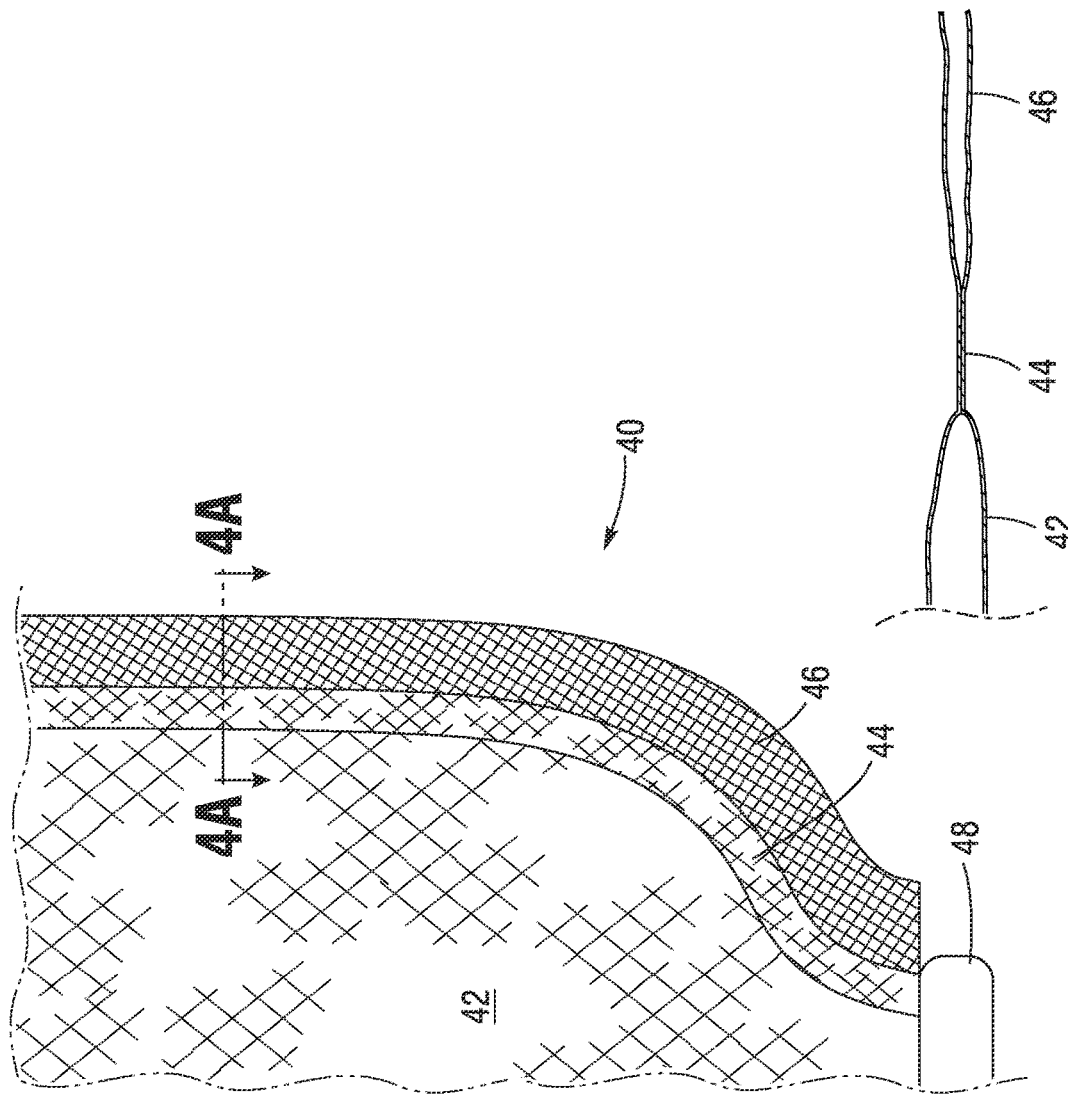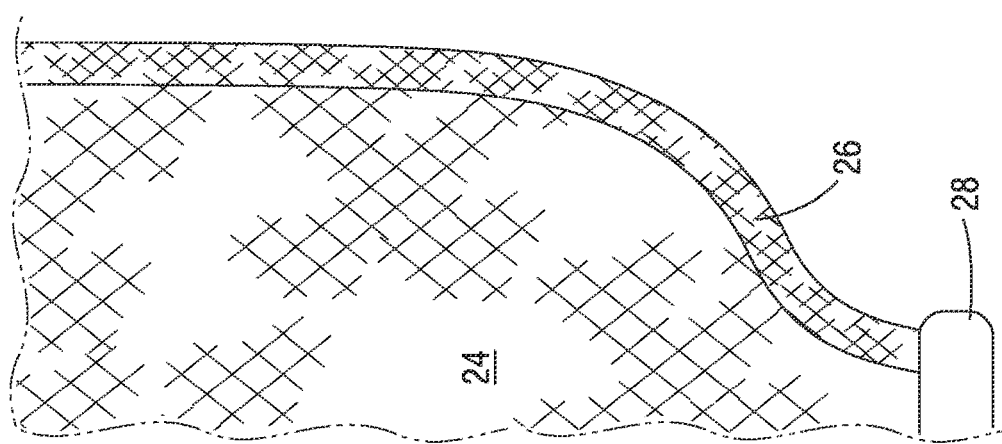

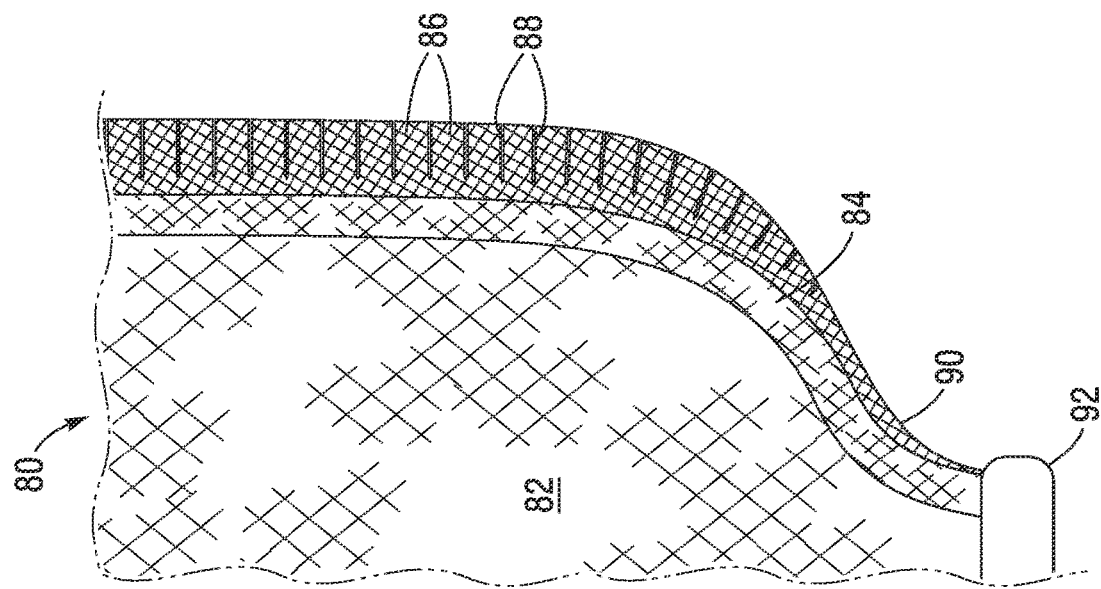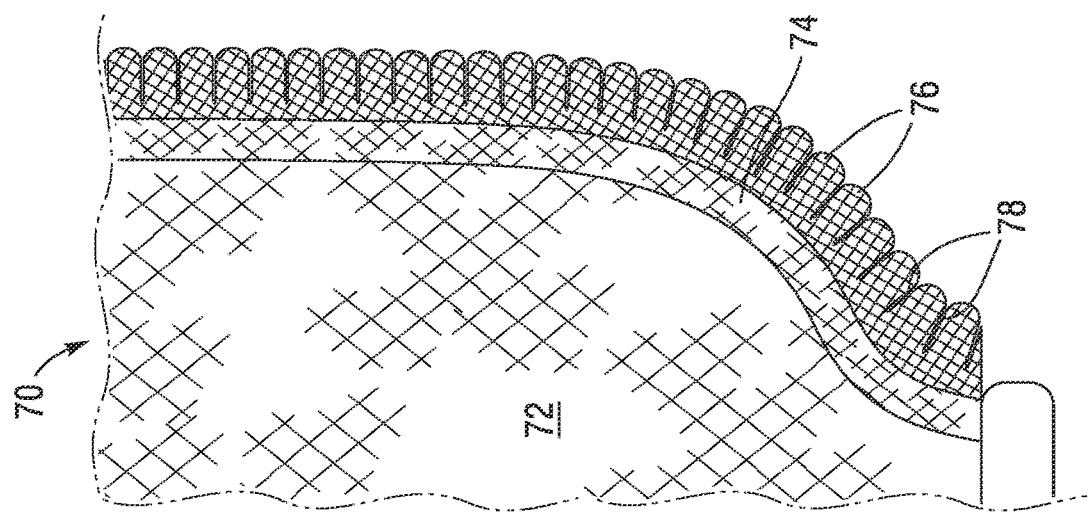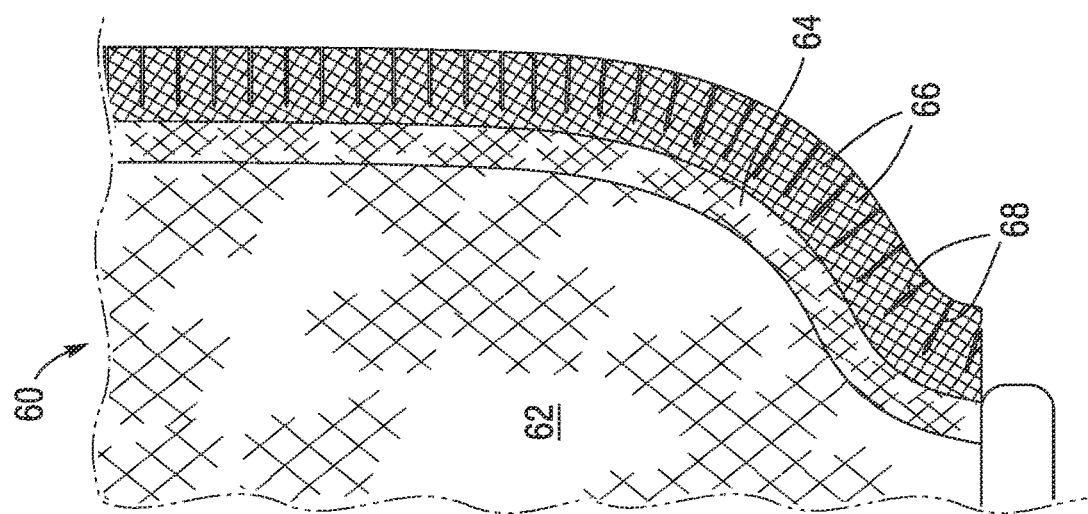

SOFT-EDGED OSTOMY BAGS

RELATED APPLICATION INFORMATION

This patent is a bypass-continuation from International PCT Patent Application No. PCT/US22/21705, filed Mar. 24, 2022 entitled, "SOFT-EDGED OSTOMY BAGS", which claims priority to U.S. Provisional Patent Application No. 63/178,714, filed Apr. 23, 2021 all of which are incorporated herein by reference in their entirety.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner have no objection to the facsimile reproduction by anyone of the patent disclosure as it appears in the Patent and Trademark Office patent files or records, but otherwise reserves all copyright and trade dress rights whatsoever.

FIELD

The present application relates to ostomy bags and, more particularly, ostomy bags configured to reduce skin irritation from relative movement when worn.

BACKGROUND

An ostomy is a surgically created opening or stoma between an internal organ and the body surface. Ostomies are often created as a part of intestinal surgery to create a new path for wastes to leave the body. An ostomy bag is often used to collect the waste that exits the stoma. Cancer, trauma, inflammatory bowel disease (IBD), bowel obstruction, infection, fecal incontinence (inability to control bowel movements) and diverticulitis (inflammation of tiny pockets that commonly form in the colon wall) are all possible reasons for ostomy. The most common types of ostomies include: "ileostomy" (which connects the ileum, the last part of the small intestine, to the skin of the abdominal wall) and "colostomy" (which connects a part of the colon, or large intestine, to the skin of the abdominal wall).

Typically, an ostomy pouch or bag includes two apposing flexible sheets, which are sealed or welded around peripheral edges to define a cavity to collect body waste. Nonwovens have been commonly used with odor barrier films to make ostomy pouches. One example is a "3-layer" ostomy pouch including two layers of odor barrier films forming the opposing sheets, and a nonwoven layer attached to the body side sheet of the ostomy pouch. The nonwoven functions as a comfort panel to give soft touch feel to users and to reduce the wet slippery feel when the user perspires. Another example is a "4-layer" ostomy pouch including two layers of odor barrier films forming the opposing sheets and two nonwoven layers, one attached to each of the sheets.

Ostomy pouches or bags come in several different styles. Closed end pouches are most commonly used by patients who have regular elimination patterns. They are discarded after one use. Open-ended pouches are left attached to the body and have an opening for draining the contents. A two-piece ostomy bag allows the user to change the bag while leaving a barrier attached to the skin. The skin barrier has a closing ring to prevent leaks if the bag is not attached. Finally, a one-piece system consists of a skin barrier and bag joined together as a single unit.

Regardless of style, ostomy bags are always formed by two apposing flexible sheets secured around their peripheries with a seam, typically welded or heat bonded. The seam extends around the edge of the bag and can be irritating to the user's skin, especially with relative movement of the bag and skin during walking or other movement.

Covers are the main solution for reducing discomfort from ostomy bags, though covers increase the thickness of the bag and a better solution is needed.

SUMMARY OF THE INVENTION

Embodiments of the present invention seek to provide a more comfortable ostomy bag that will not irritate the skin from relative movement.

In one embodiment, and ostomy bag, comprises a pair of flexible flat sheets of liquid impermeable material bonded together at juxtaposed edges at a peripheral seam to form a pouch with an inner cavity. A soft outer edge radially outward of the seam is formed by outward extensions of the sheets that form loose flaps. The ostomy bag further has an inlet opening and stoma seal formed through one of the flat sheets and open to the inner cavity.

The outward extensions may be continuous around a periphery of the bag. The continuous outward extensions may have varying radial dimensions around the outer edge, such as a scalloped configuration with varying radial dimensions around the outer edge. The continuous outward extensions may not be connected to each other around the outer edge.

The ostomy bag pouch may have a long dimension and a short dimension perpendicular to the long dimension, and wherein the soft outer edge has a radial dimension of between 5-15% of the short dimension. An outlet may be included at one end of the long dimension that interrupts the peripheral seam.

The outward extensions may have scalloped configurations with varying radial dimensions around the outer edge. The ostomy bag may further include an outlet at one end that interrupts the peripheral seam. In one embodiment, wherein the outward extensions have generally constant radial dimensions around the outer edge except close to the outlet where they gradually taper down in radial dimension.

Another disclosed ostomy bag comprises a pair of flexible flat sheets of liquid impermeable material bonded together at juxtaposed edges at a peripheral seam to form a pouch with an inner cavity. A soft outer edge radially outward of the seam is formed by outward extensions of the sheets that are slit radially to form finger-like projections. The ostomy bag further has an inlet opening and stoma seal formed through one of the flat sheets and open to the inner cavity.

The soft outer edge may have a continuous radial dimension around the outer edge, or a varying radial dimensions around the outer edge, such as a scalloped configuration.

In one embodiment, the outward extensions are not connected to each other around the outer edge. The pouch may have a long dimension and a short dimension perpendicular to the long dimension, and wherein the soft outer edge has a radial dimension of between 5-15% of the short dimension.

The finger-like projections may be rectangular in shape, or may each have a rounded outer end.

The ostomy bag may further include an outlet at one end that interrupts the peripheral seam. In one embodiment, wherein the outward extensions have generally constant radial dimensions around the outer edge except close to the outlet where they gradually taper down in radial dimension.

BRIEF DESCRIPTION OF THE DRAWINGS

FIG. 1 is a plan view of an ostomy bag of the prior art for use in a two-piece system;

FIG. 2 is a view of the ostomy bag of the prior art being held by a user adjacent a stoma to which the bag attaches;

FIG. 3 is a close-up of one edge of the ostomy bag illustrating a welded seam;

FIG. 4 is a close-up of a portion of an ostomy bag of the present application having a soft edge, and FIG. 4A is a sectional view through the edge;

FIGS. 6A-6C are close-ups of portions of alternative ostomy bags of the present application showing different soft edges.

DETAILED DESCRIPTION OF A PREFERRED EMBODIMENT

Figure 5:
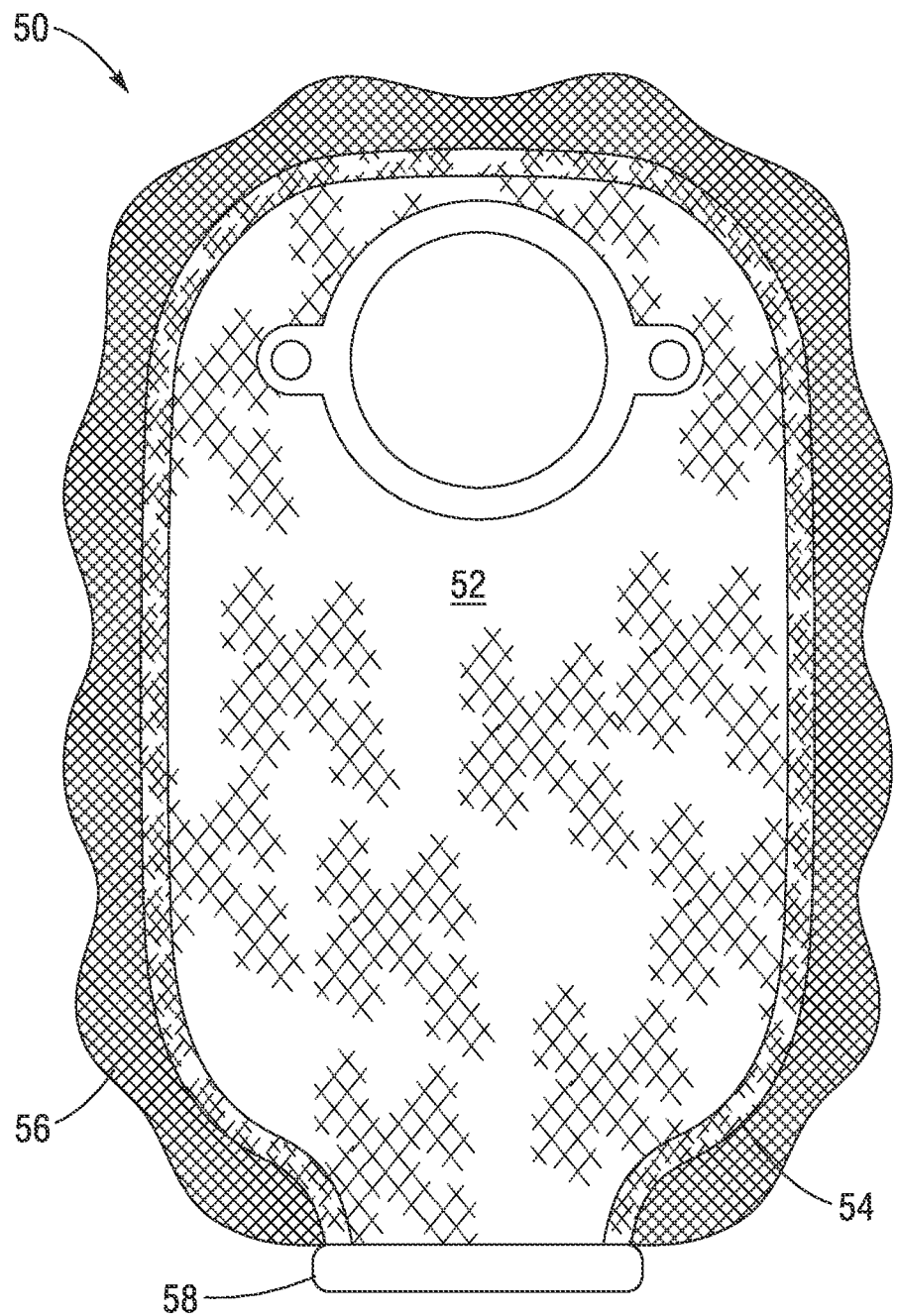
FIG. 5 is a plan view of an embodiment of an ostomy bag of the present application showing a scalloped outer edge.

The present application provides an ostomy bag that will not irritate the skin from relative movement. The embodiments described herein may be implemented on a variety of different ostomy bags, though a closed bag for a two-piece system is illustrated.

FIG. 1 is a plan view of an ostomy pouch or bag 20 of the prior art for use in a two-piece system, and FIG. 2 is a view of the ostomy bag being held by a user adjacent a skin barrier 22 to which the bag attaches. The ostomy bag 20 defines a pouch formed by two apposing generally flat flexible sheets 24 held together by a peripheral seam 26. The illustrated bag 20 has a generally rounded rectangle configuration, and the seam 26 is usually interrupted at a lower end by an outlet 28. Although not shown, the outlet 28 may be closed and selectively opened when the bag needs to be evacuated. However, in so-called closed-ended pouches the entire disposable bag 20 is removed once full and replaced with a new one. An inlet opening 30 defined by a generally flat circular sealing ring 32 is mounted across one of the flexible sheets 22.

FIG. 2 shows how the user connects the circular sealing ring 32 to the mating skin barrier 22. There are a number of different types of seals used for ostomy bags, and present application encompasses all of them. The end result is that the patient's stoma 34, which opens to a portion of the intestine, is placed in fluid communication with the inlet opening 30 of the ostomy bag 20. The bag 20 remains flat against the patient's stomach or abdomen until filled with fluid, at which point it may be removed for emptying. The size of the stoma 34 may change over time, necessitating a change in ostomy bags 20 with differently-sized openings 30.

A typical ostomy bag 20 construction has two flexible sheets 24 made of gas- and liquid impermeable plastic or foil-material (for example of polyethylene (PE), polyvinylchloride (PVC) or ethylene-vinyl-acetate (EVA)) that is welded or glued around the edges to form the seam 26. A material that is now used commercially, a plasticized poly (vinylidene chloride) ("PVDC"), has a low oxygen permeability so as to reduce unpleasant odor as an ostomy patient's day progresses. Another suggested material is at least one layer of an oriented liquid crystal polymer ("LCP").

The presently disclosed ostomy bags may be formed of a variety of different materials, with modifications to the seam 26 to increase patient comfort. Ostomy bags 20 come in different sizes, typically measured in volumetric capacity, from 500 ml up to 1200 ml for high output needs. The pouches formed by the flexible sheets 24 are generally oval or rounded rectangular in shape, with a long dimension at one end of which is the outlet 28 and a short dimension perpendicular to the long dimension. Typically, the long dimension is between about 9-14 inches and a short dimension is between about 5-9 inches.

FIG. 3 is a close-up of one edge of the ostomy bag illustrating the seam 26. The seam 26 has a width typically ranging between 3-7 mm, and has a thickness approximately equal to the combined thickness of the two sheets 24. Due to the weld or adhesive that forms the seam 26, it is relatively stiff with a somewhat sharp outer edge. Movement of the wearer, such as in simply walking, often causes the seam 26 to chafe at the wearer's skin, sometimes leaving abrasions or even cuts.

FIG. 4 is a close-up of a portion of an ostomy bag 40 of the present application comprising two apposing sheets 42 secured together around their adjoining peripheries at a seam 44, and having a soft outer edge 46 interrupted by an outlet 48, and FIG. 4A is a sectional view through the edge. The soft edge 46 may be formed by extensions of the two sheets 42 past the seam 44 in two loose flaps that are continuous around a periphery of the bag 40, except where interrupted by the outlet 48. By recessing the seam 44 within the outer boundary of the bag 40, patient comfort is greatly enhanced. That is, relative movement of the wearer may cause the soft edge 46 to rub on the skin, but the lack of any glued or welded outer contact point eliminates the chances of abrasions or cuts.

The radial (outward) dimensions of the soft outer edge 46 may vary, and typically range between 5-15% of the short dimension of the typical bag. For instance, if the bag has a short dimension of 5 inches, the soft outer edge 46 may be between ¼ and ¾ of an inch in radial dimension. In absolute terms, the soft outer edge 46 may be between 0.25-1.25 of an inch in radial dimension. It should be understood that the term "radial" refers to a dimension extending outward from a central axis or axes defined by the pouch, as measured perpendicularly through a tangent to the outer edge 46 at any one point, as the pouches are not typically circular.

FIG. 5 is a plan view of an embodiment of an ostomy bag 50 of the present application constructed with two apposing sheets 52 secured together around their adjoining peripheries at a seam 54, and having a scalloped soft outer edge 56 interrupted by an outlet 58. The soft outer edge 56 may be formed in any manner described herein, such as by extending the two sheets 52 outside of the seam 54 in loose flaps that are continuous around a periphery of the bag 50. The scalloped shape of the outer edge 56 helps further prevent abrasions and increase wearer comfort.

FIGS. 6A-6C are close-ups of portions of alternative ostomy bags of the present application showing different soft edges. FIG. 6A shows a bag 60 constructed with two apposing sheets 62 secured together around their adjoining peripheries at a seam 64, and having a soft outer edge exclusive of an outlet (not numbered) formed by a plurality of rectangular finger-like projections 66 with generally radial slits 68 therebetween. The outer edge may be two loose extensions or flaps of the apposing sheets 62. However, the two sheet extensions or flaps may be secured together with glue or the like, and adding the slits 68 to form the separate projections 66 will break up the otherwise sharp continuous outer edge, which may be enough to reduce discomfort.

FIG. 6B shows a bag 70 constructed with two apposing sheets 72 joined together at a seam 74, with a soft outer edge exclusive of an outlet (not numbered) formed by a plurality of finger-like projections 76 with generally radial slits 78 therebetween. Again, the outer edge may be two loose extensions or flaps of the apposing sheets 72, either secured together or not. In addition to the separate fingers 76, which softens the edge, each finger has a rounded outer end to further reduce any corners which might create friction with the skin.

Finally, FIG. 6C shows a bag 80 constructed with two apposing sheets 82 secured together around their adjoining peripheries at a seam 84. A soft outer edge projecting radially outward from the seam 84 is formed by a plurality of finger-like projections 86 with generally radial slits 88 therebetween. The outer edge may be two loose extensions or flaps of the apposing sheets 82, or the two flaps may be adhered together. Rather than extending the soft outer edge around the entire periphery of the bag 80 in a constant radial dimension, exclusive of an outlet 92, portions may be gradually reduced in size, such as at a tapered region 90 leading to the outlet 92. It should be noted that the tapered region 90 leading to the outlet 92 may also be integrated into the bags 40, 50 that have soft edges without radial slits.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

The invention claimed is:

1. An ostomy bag, comprising:
a pair of flexible flat sheets of liquid impermeable material bonded together at juxtaposed edges at a peripheral seam to form a pouch with an inner cavity, and a soft outer edge radially outward of the seam formed by disconnected outward extensions of the sheets that form loose flaps, the ostomy bag further having an inlet opening and stoma seal formed through one of the flat sheets and open to the inner cavity, wherein the pouch has a long dimension and a short dimension perpendicular to the long dimension, and wherein the soft outer edge has a radial dimension of between 5-15% of the short dimension.

2. The ostomy bag of claim 1, wherein the outward extensions are continuous around a periphery of the bag.

3. The ostomy bag of claim 2, wherein the continuous outward extensions have varying radial dimensions around the outer edge.

4. The ostomy bag of claim 2, wherein the continuous outward extensions have scalloped configurations with varying radial dimensions around the outer edge.

5. The ostomy bag of claim 2, wherein the continuous outward extensions are not connected to each other around the outer edge.

6. The ostomy bag of claim 1, further including an outlet at one end of the long dimension that interrupts the peripheral seam.

7. The ostomy bag of claim 1, further including an outlet at one end that interrupts the peripheral seam.

8. The ostomy bag of claim 7, wherein the outward extensions have generally constant radial dimensions around the outer edge except close to the outlet where they gradually taper down in radial dimension.

9. The ostomy bag of claim 1, wherein the liquid impermeable material is also gas-impermeable.

10. The ostomy bag of claim 1, wherein the liquid impermeable material is selected from the group consisting of: polyethylene (PE), polyvinyl-chloride (PVC), ethylene-vinyl-acetate (EVA), plasticized poly(vinylidene chloride) (PVDC), and an oriented liquid crystal polymer (LCP).

11. An ostomy bag, comprising:
a pair of flexible flat sheets of liquid impermeable material bonded together at juxtaposed edges at a peripheral seam to form a pouch with an inner cavity, and a soft outer edge radially outward of the seam formed by disconnected outward extensions of the sheets that form loose flaps, the ostomy bag further having an inlet opening and stoma seal formed through one of the flat sheets and open to the inner cavity, wherein the outward extensions have scalloped configurations with varying radial dimensions around the outer edge.

12. An ostomy bag, comprising:
a pair of flexible flat sheets of liquid impermeable material bonded together at juxtaposed edges at a peripheral seam to form a pouch with an inner cavity, and a soft outer edge radially outward of the seam formed by outward extensions of the sheets that are slit radially to form finger-like projections, the ostomy bag further having an inlet opening and stoma seal formed through one of the flat sheets and open to the inner cavity.

13. The ostomy bag of claim 12, wherein the soft outer edge has a continuous radial dimension around the outer edge.

14. The ostomy bag of claim 12, wherein the soft outer edge has varying radial dimensions around the outer edge.

15. The ostomy bag of claim 14, wherein the varying radial dimensions form a scalloped outer edge.

16. The ostomy bag of claim 12, wherein the outward extensions are not connected to each other around the outer edge.

17. The ostomy bag of claim 12, wherein the pouch has a long dimension and a short dimension perpendicular to the long dimension, and wherein the soft outer edge has a radial dimension of between 5-15% of the short dimension.

18. The ostomy bag of claim 12, wherein the finger-like projections are rectangular in shape.

19. The ostomy bag of claim 12, wherein the finger-like projections each has a rounded outer end.

20. The ostomy bag of claim 12, further including an outlet at one end that interrupts the peripheral seam.

21. The ostomy bag of claim 20, wherein the outward extensions have generally constant radial dimensions around the outer edge except close to the outlet where they gradually taper down in radial dimension.

22. The ostomy bag of claim 12, wherein the liquid impermeable material is also gas-impermeable.

23. The ostomy bag of claim 12, wherein the liquid impermeable material is selected from the group consisting of: polyethylene (PE), polyvinyl-chloride (PVC), ethylene-vinyl-acetate (EVA), plasticized poly(vinylidene chloride) (PVDC), and an oriented liquid crystal polymer (LCP).

* * * * *